(12) United States Patent
Ikeda et al.

(10) Patent No.: US 7,722,532 B2
(45) Date of Patent: May 25, 2010

(54) ELECTRIC BENDING ENDOSCOPE

(75) Inventors: Yuichi Ikeda, Tama (JP); Toshinari Maeda, Hachioji (JP); Haruhiko Ueno, Hachioji (JP); Keiichi Arai, Hachioji (JP); Takayasu Miyagi, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 188 days.

(21) Appl. No.: 10/673,122

(22) Filed: Sep. 26, 2003

(65) Prior Publication Data
US 2004/0073083 A1 Apr. 15, 2004

(30) Foreign Application Priority Data
Sep. 30, 2002 (JP) ............................ 2002-287851

(51) Int. Cl.
*A61B 1/00* (2006.01)
(52) U.S. Cl. .................... 600/146; 600/102; 600/118; 600/152
(58) Field of Classification Search ............. 600/146, 600/152
See application file for complete search history.

(56) References Cited

U.S. PATENT DOCUMENTS

| | | | | |
|---|---|---|---|---|
| 4,919,112 A | * | 4/1990 | Siegmund | 600/136 |
| 4,982,725 A | * | 1/1991 | Hibino et al. | 600/117 |
| 5,400,769 A | * | 3/1995 | Tanii et al. | 600/152 |
| 5,609,563 A | * | 3/1997 | Suzuki et al. | 600/118 |
| 5,634,466 A | * | 6/1997 | Gruner | 600/459 |
| 5,667,476 A | * | 9/1997 | Frassica et al. | 600/149 |
| 6,371,907 B1 | * | 4/2002 | Hasegawa et al. | 600/146 |
| 6,529,620 B2 | * | 3/2003 | Thompson | 382/141 |
| 6,537,206 B2 | * | 3/2003 | Takada | 600/114 |
| 6,569,084 B1 | * | 5/2003 | Mizuno et al. | 600/102 |
| 6,669,629 B2 | * | 12/2003 | Matsui | 600/152 |
| 6,793,622 B2 | * | 9/2004 | Konomura et al. | 600/152 |
| 6,802,809 B2 | * | 10/2004 | Okada | 600/146 |

FOREIGN PATENT DOCUMENTS

| JP | 2-159243 | 6/1990 |
|---|---|---|
| JP | 4-256724 | 9/1992 |

* cited by examiner

*Primary Examiner*—Matthew J Kasztejna
(74) *Attorney, Agent, or Firm*—Scully, Scott, Murphy & Presser, P.C.

(57) ABSTRACT

An electric bending endoscope comprises a bending portion arranged to an inserting portion, a bending driving unit and a buffering member. The bending driving unit bends the bending portion, and includes a motor, a first unit and a second unit. The motor generates driving force for bending the bending portion. The first unit holds the motor. The second unit includes a driving force transmitting member. The buffering member connects the first unit to an outer member of the inserting portion, a connecting code and a switch. The buffering member absorbs external force generated during the operation of the electric bending endoscope.

3 Claims, 8 Drawing Sheets

ELECTRIC BENDING ENDOSCOPE

This application claims benefits of Japanese Application No. 2002-287851 filed in Japan on Sep. 30, 2002, the contents of which are incorporated by this reference.

BACKGROUND OF THE INVENTION

1. Field of the Invention

The present invention relates to an electric bending endoscope which electrically bends a bending portion of an inserting portion.

2. Description of the Related Art

Recently, an endoscope is widely used. Various curing treatments are performed by inserting an elongated inserting portion in the celom so as to observe the organ in the celom or by using a treatment tool inserted in a therapeutic instrument channel as needed. In the industrial field, the endoscope observes and examines inner scratches and corrosion of a steam generator, a turbine, an engine and a chemical plant by inserting an elongated inserting portion.

The endoscope has a bending portion which is freely bent on a base end side of an edge portion in the elongated inserting portion. Further, the endoscope receives an instruction as the amount of bending, corresponding to a bending position or a bending speed of the bending portion, by means for inputting a bending operation such as a bending operation lever or a joystick arranged to an operating portion. In the endoscope, a bending operation wire is mechanically stretched or contracted based on the amount of bending inputted as the instruction so as to bend the bending portion.

The above-mentioned endoscope includes an electric bending endoscope in views of the operability. For example, Japanese Unexamined Patent Application Publication No. 2-159243 discloses one of the above-mentioned electric bending endoscopes, in which a built-in motor as bending driving means is controlled for rotation, the motor's driving force enables a bending operation wire to stretch or contract, and the bending portion is electrically bent.

In the electric bending endoscope disclosed in Japanese Unexamined Patent Application Publication No. 2-159243, a bending operation device unit is integrally formed by connecting, to a main frame as a main frame member and a subframe, the motor as the bending operation means, a sprocket as a rotator for the stretch operation which transmits the motor's driving force to the bending operation wire, and the entire bending and stretch mechanism forming portions such as a transmission gear train. Further, the bending operation device unit is enclosed in the operating portion.

Similarly to the electric bending endoscope disclosed in Japanese Unexamined Patent Application Publication No. 2-159243, Japanese Unexamined Patent Application Publication No. 4-256724 discloses an electric bending endoscope in which a bending operation device unit is integrally formed by connecting, to a main frame and the like, a bending and stretch mechanism forming portions and the bending operation device unit is enclosed in the operating portion. The electric bending endoscope disclosed in Japanese Unexamined Patent Application Publication No. 4-256724 accomplishes an object of the present invention to provide the electric bending endoscope which can accurately sets a locking state and a free state with the compact size, light weight, and simple structure.

SUMMARY OF THE INVENTION

Briefly, according to the present invention, an electric bending endoscope comprises a bending portion arranged to an inserting portion, a bending driving unit and a buffering member. The bending driving unit bends the bending portion, and includes a motor, a first unit and a second unit. The motor generates driving force for bending the bending portion. The first unit holds the motor. The second unit includes a driving force transmitting member. The buffering member connects the first unit to an outer member of the inserting portion, a connecting cord and a switch. The buffering member absorbs external force generated during the operation of the electric bending endoscope.

The objects and advantages of the present invention will become apparent from the following detailed explanation.

DETAILED DESCRIPTION OF THE PREFERRED EMBODIMENTS

Hereinbelow, a description is given of embodiments of the present invention with reference to the drawings.

First Embodiment

Figure 1:
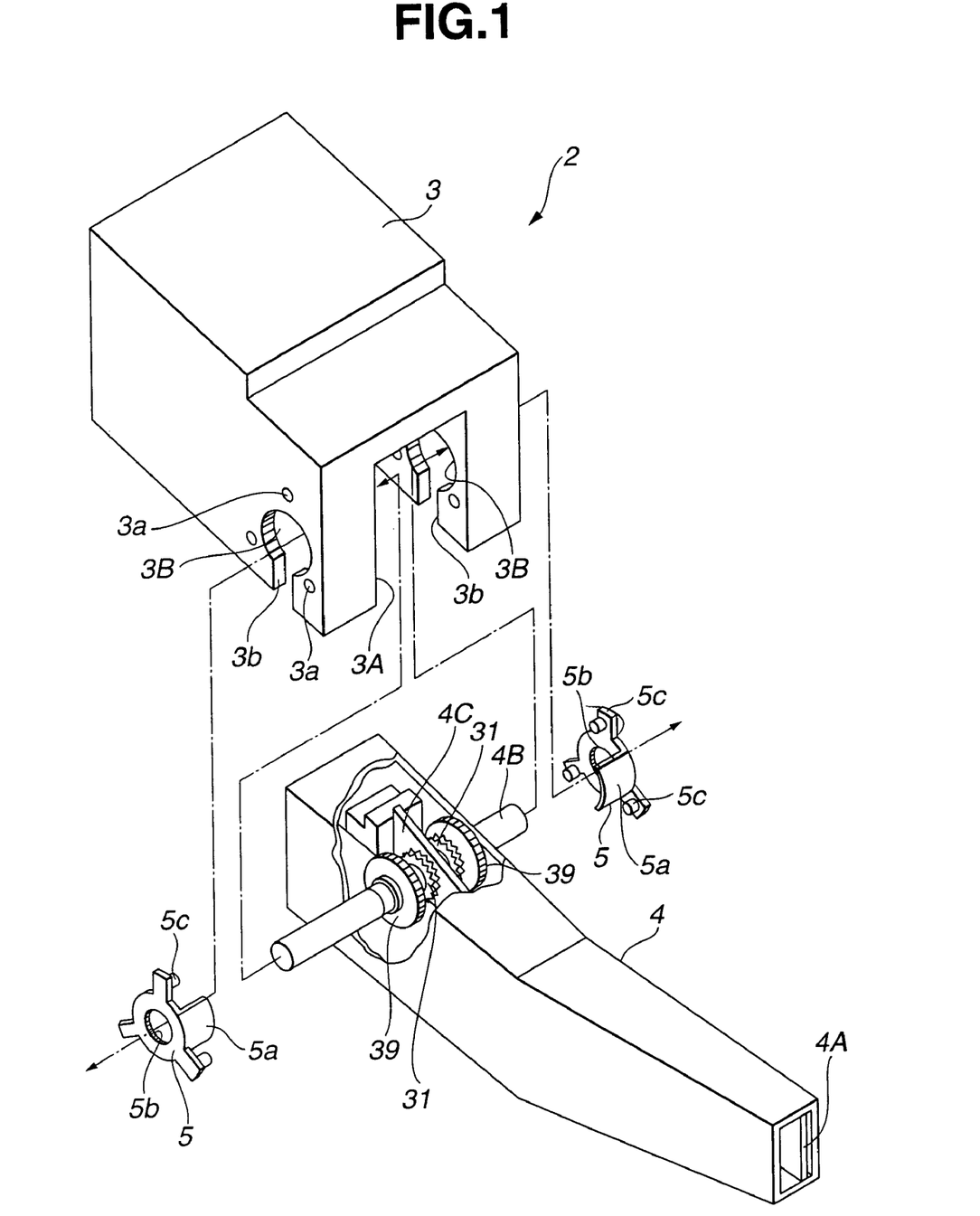
FIG. 1 is an exploded perspective view showing the schematic structure of an electric bending endoscope according to a first embodiment of the present invention.
Figure 2:
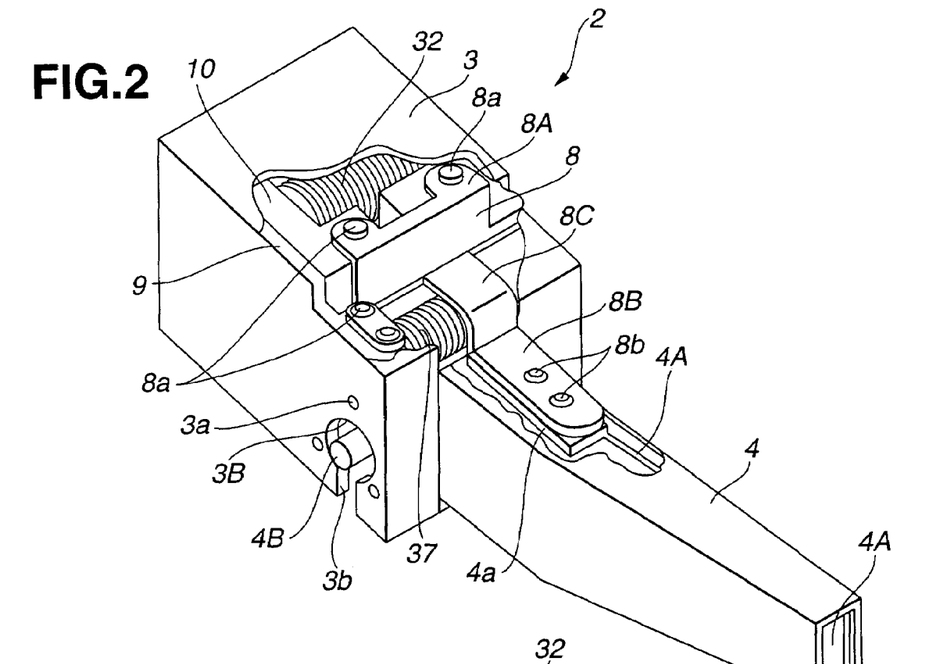
FIG. 2 is a perspective view schematically showing the electric bending endoscope shown in FIG. 1 after assembling, including a cut-off part.
Figure 3:
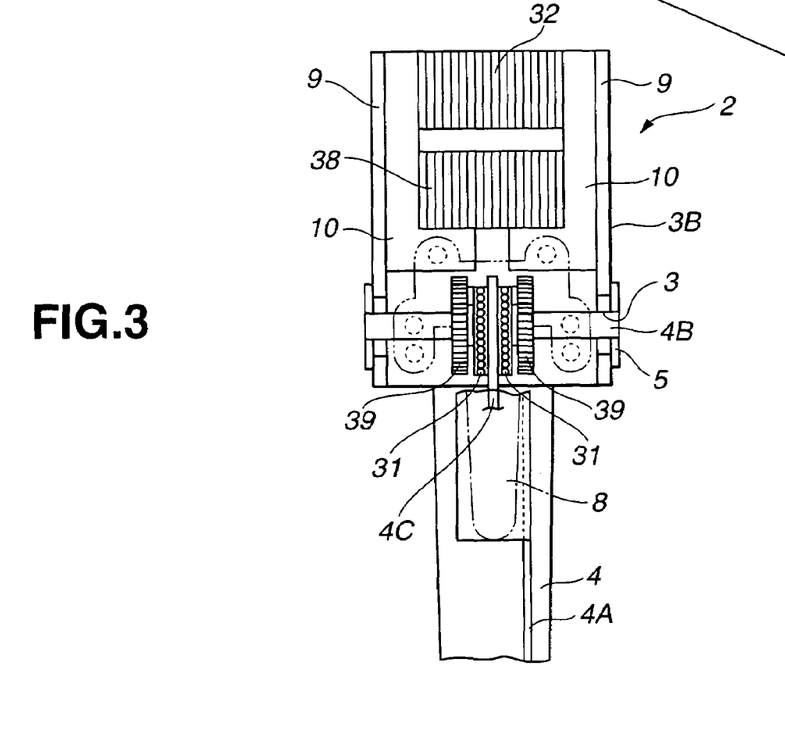
FIG. 3 is a plan view showing the electric bending endoscope shown in FIG. 2.
Figure 4:
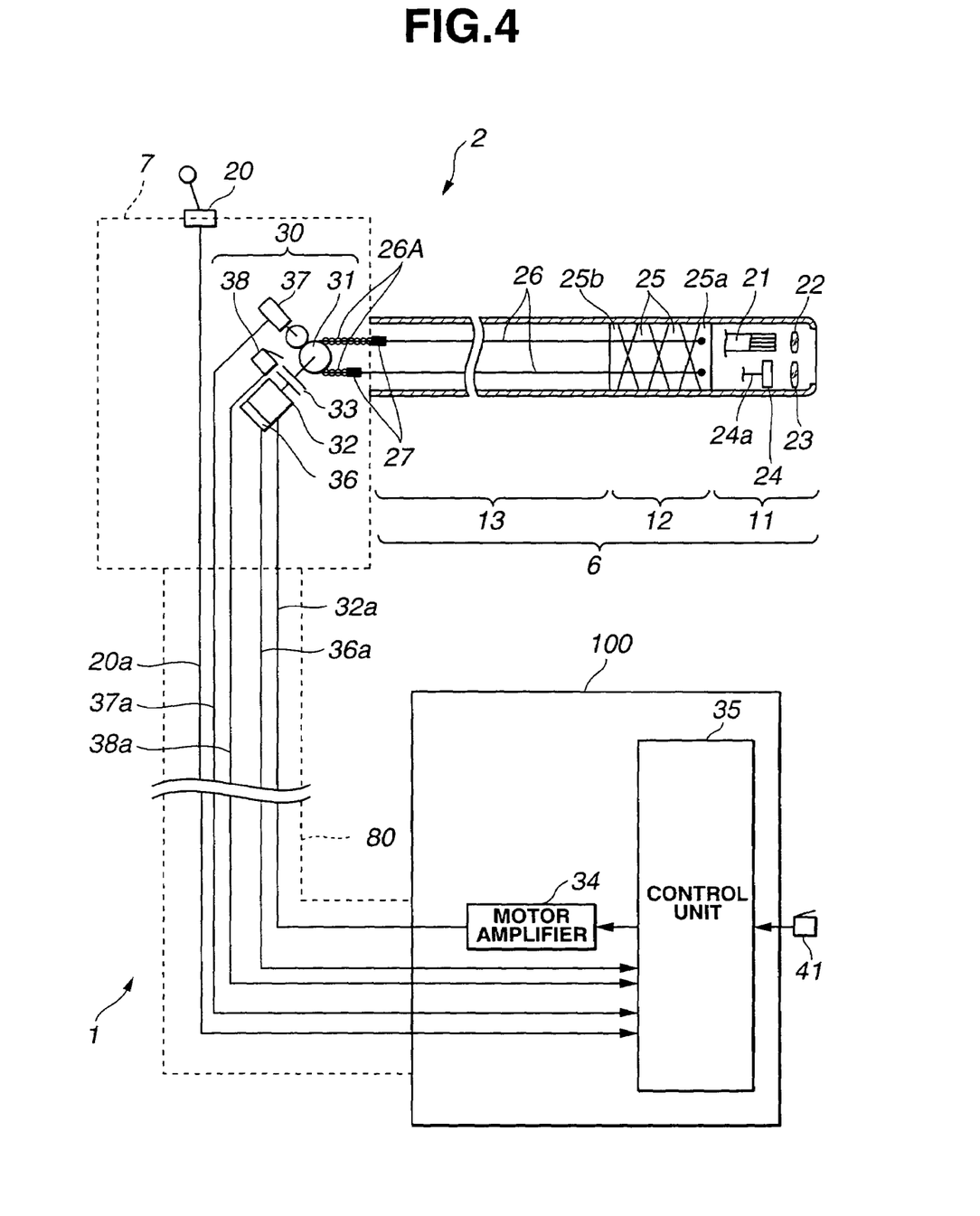
FIG. 4 is a diagram showing the entire structure of an electric bending endoscope apparatus having the electric bending endoscope according to the first embodiment.
Figure 5:
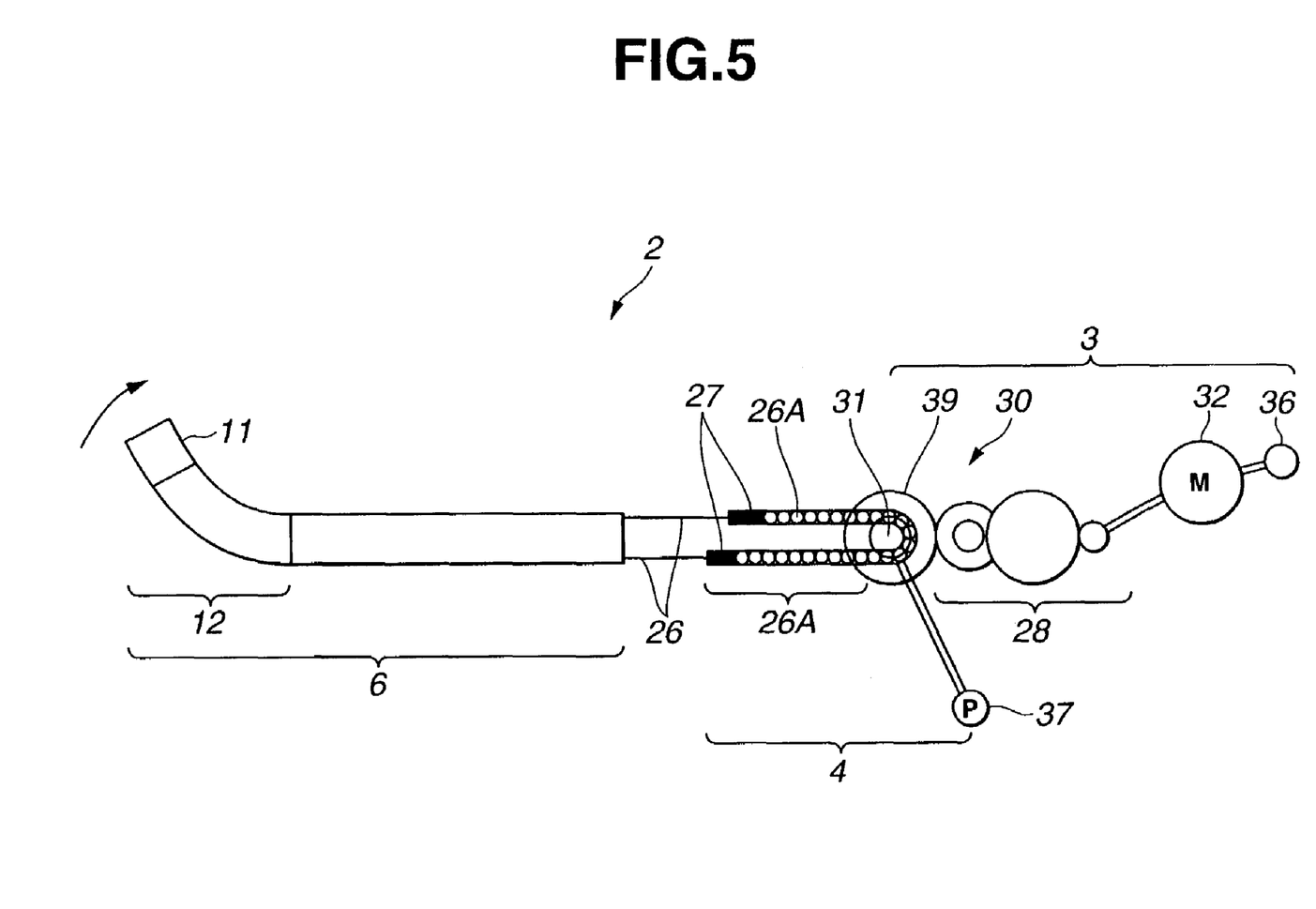
FIG. 5 is a diagram schematically showing main portions of the electric bending endoscope shown in FIG. 4 formed as units.
Figure 6:
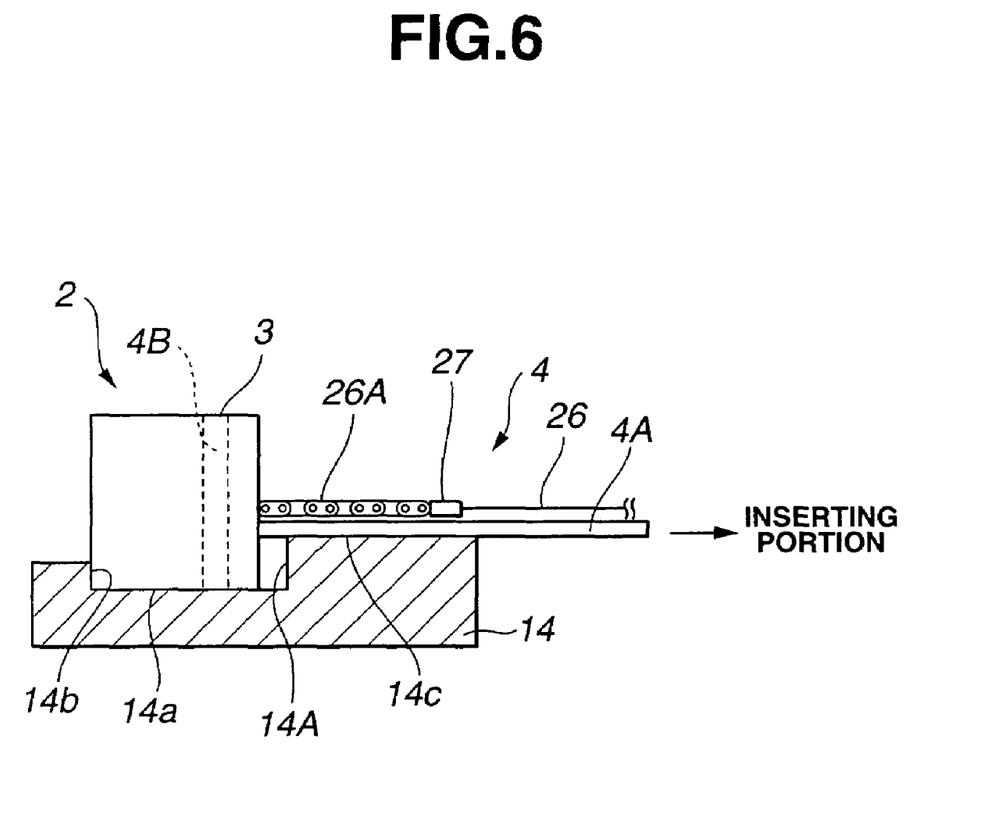
FIG. 6 is a cross-sectional view showing an attaching state of a gear box and a bending and stretch mechanism portion by using a tool, describing the operation, according to the first embodiment.
Figure 7:
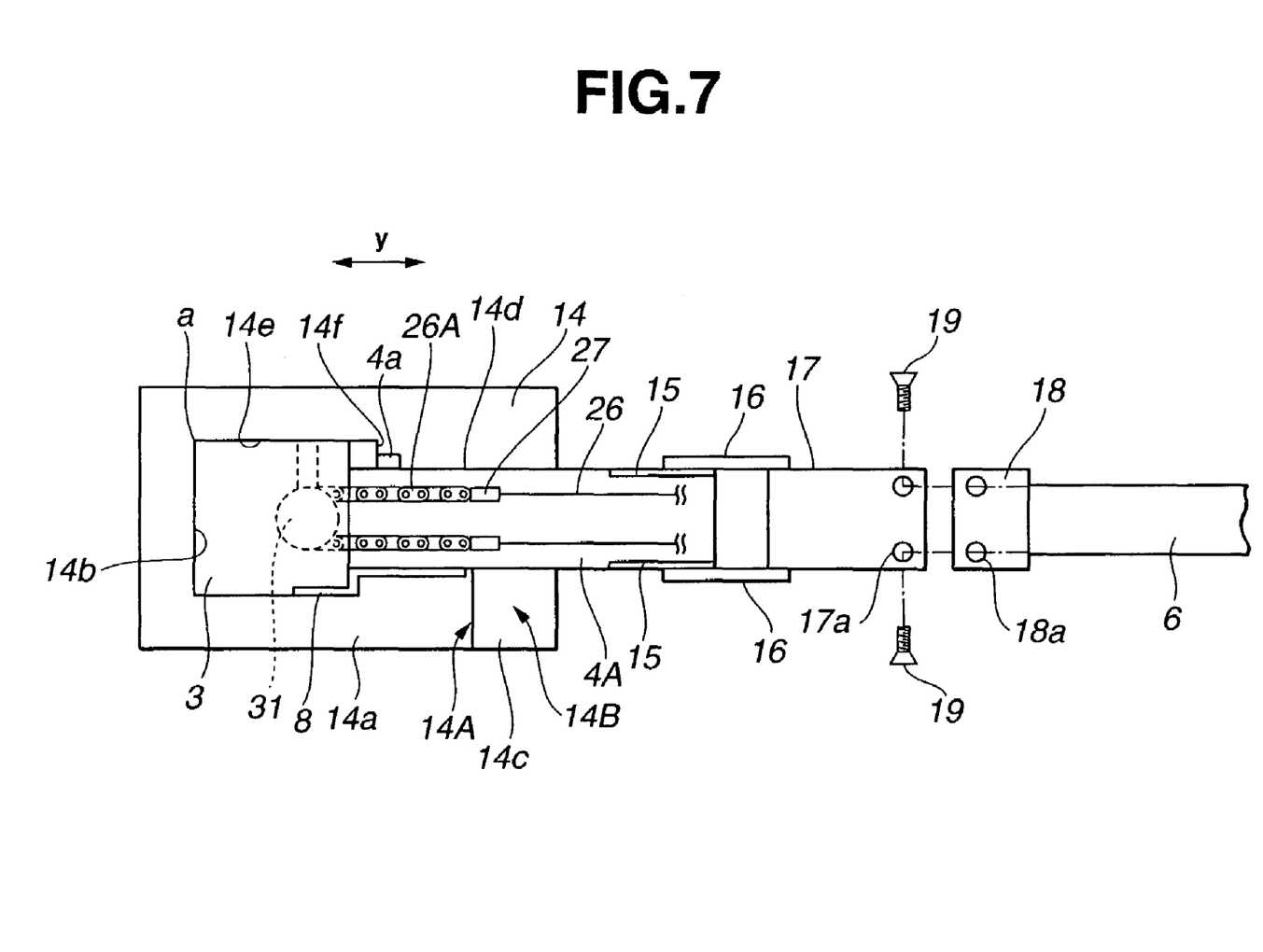
FIG. 7 is a plan view showing an attaching state of the bending and stretch mechanism portion including an inserting portion, describing the operation, according to the first embodiment.

FIGS. 1 to 7 show an electric bending endoscope according to a first embodiment of the present invention. FIG. 1 is an exploded perspective view showing the schematic structure of an electric bending endoscope according to the first embodiment. FIG. 2 is a perspective view schematically showing the electric bending endoscope shown in FIG. 1 after assembling, including a cut-off part. FIG. 3 is a plan view showing the electric bending endoscope shown in FIG. 2. FIG. 4 is a diagram showing the entire structure of an electric bending endoscope apparatus having the electric bending endoscope according to the first embodiment. FIG. 5 is a diagram schematically showing a main portion of the electric bending endoscope shown in FIG. 4 as a unit. FIGS. 6 and 7 are diagrams for explaining a method for attaching a gear box and a bending and stretch mechanism portion in the electric bending endoscope. FIG. 6 is a cross-sectional view showing an attaching state of the gear box and the bending and stretch mechanism portion by using a tool, and describing the operation. FIG. 7 is a plan view showing an attaching state of the bending and stretch mechanism portion including an inserting portion, and describing the operation.

First, a description is given of the system structure of an electric bending endoscope apparatus having the electric bending endoscope of the present invention with reference to FIG. 4.

Referring to FIG. 4, an electric bending endoscope apparatus 1 having an electric bending endoscope 2 comprises a bending driving portion 30 for electrically bending a bending portion 12 described later, arranged to the edge of an inserting portion 6, a light source device (not shown) for supplying illumination light to the electric bending endoscope 2, a video processor (not shown) for performing signal processing for image pick-up means incorporated in the electric bending endoscope 2, and a bending control device 100 for controlling the driving operation of the bending driving portion in the electric bending endoscope 2. Incidentally, the video processor is connected to a monitor (not shown), outputs a video signal to the monitor, and displays an endoscope image.

Figure 10:
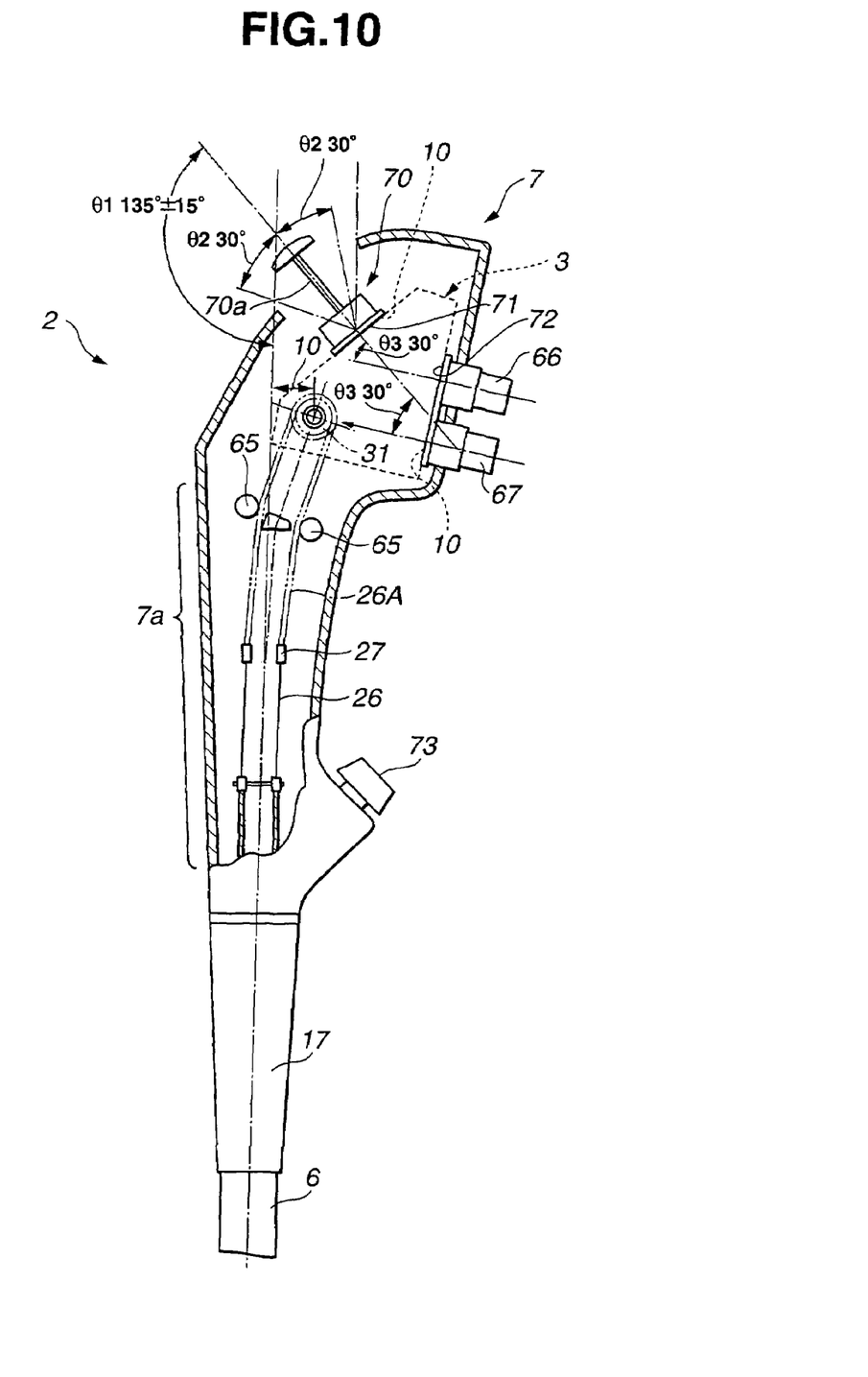
FIG. 10 is a cross-sectional view showing the structure of an electric bending endoscope, further showing the layout of a bending and stretch mechanism and switches in an operating portion provided for the electric bending endoscope, including a cut-off part according to a third embodiment of the present invention.

The electric bending endoscope 2 is continuously arranged to a base end of the inserting portion 6 and comprises an operating portion 7 which commonly functions as a grip portion 7a (refer to FIG. 10). The electric bending endoscope 2 has a soft universal cord 80 extended from a side portion at the operating portion 7.

A light guide or various signal cables (which are not shown) are inserted in the universal cord 80. A connector portion (not shown) is arranged to an end portion of the universal cord 80. Connecting cables from the light source device and the video processor (not shown) and a connecting cable from the bending control device 100 are connected detachably to the universal cord 80.

Continuously arranged to the inserting portion 6 of the electric bending endoscope 2 is a hard edge portion 11 arranged to the edge thereof, a bending portion 12 which is arranged to a base end side of the edge portion 11 and is freely bent, and a flexible tube portion 13 which is long and flexible and is arranged to a base end side of the bending portion 12.

The operating portion 7 of the electric bending endoscope 2 includes the grip portion 7a (refer to FIG. 10) as a portion which is gripped by a user. In the operating portion 7, a plurality of video switches (not shown) for remote control of the video processor are arranged at an upper portion of the grip portion 7a. Arranged to a side surface of the operating portion 7 are an air and water supply button 66 for operating the air and water supply operation and a suction button 67 for a suction operation (refer to FIG. 10).

Further, a therapeutic instrument inserting slit 73 (refer to FIG. 10) for inserting a therapeutic instrument such as a biopsy clamp is arranged near a front end of the grip portion 7a of the operating portion 7. The therapeutic instrument inserting slit 73 is connected to a channel for inserting the therapeutic instrument (not shown). A therapeutic instrument such as a clamp (not shown) is inserted in the therapeutic instrument inserting slit 73, the edge of the therapeutic instrument is projected from the opening of the channel formed to the edge portion 11 via the channel for inserting the therapeutic instrument for biopsy, and the biopsy is performed.

The operating portion 7 comprises a bending operation input portion 20 for inputting the operation for bending the bending portion 12 such as a joystick and a track ball.

Further, a specific description is given of the electric bending endoscope 2. A light guide 21 for transmitting the illumination light is inserted in the inserting portion 6 in the electric bending endoscope 2. The light guide 21 reaches the connector portion of the universal cord 80 via the operating portion 7 from the base end side so as to transmit the illumination light from a light source lamp (not shown) arranged in the light source device. The illumination light transmitted from the light guide 21 illuminates a subject such as an affected part of the body from an edge surface of an illumination window (not shown) fixed to the edge portion 11 of the inserting portion via an illumination optical system 22.

An illuminated subject image, namely, a subject image is captured from an observation window (not shown) arranged adjacently to the illumination window. The captured subject image is picked up by an image pick-up device 24 such as a CCD (Charge-Coupled Device) via an objective optical system 23 and is photoelectrically converted into an image pick-up signal. The image pick-up signal is transmitted via a signal cable 24a extending from the image pick-up device 24, reaches the video connector of the universal cord 80 via the operating portion 7, and is outputted to the video processor (not shown) via the connecting cable. The video processor processes the image pick-up signal from the image pick-up device 24 in the electric bending endoscope 2, generates a standard video signal, and displays the endoscope image on a monitor.

A bending piece 25a at the front end of rotatably connected bending pieces 25 forming the bending portion 12 is connected to a base end portion of the edge portion 11 of the inserting portion in the electric bending endoscope 2. A bending piece 25b at the final end of the bending pieces 25 is connected to an edge side of the flexible portion 13.

A bending operation wire 26 is inserted in the inserting portion 6 to bend the bending portion 12 in the vertical and horizontal directions of an observation field of view. The edge of the bending operation wire 26 is fixed and held to the bending piece 25a at the front end by wax at positions corresponding to the vertical and horizontal directions of the bending portion 12. Referring to FIG. 5, the bending portion 12 is bent in a desired direction and the edge portion 11 is positioned in a desired direction by stretching or contracting the bending operation wire 26 in accordance with the directions.

The bending operation wire 26 is connected to a chain 26A via a connecting portion 27 in a bending and stretch mechanism portion 4, and is stretched or contracted by the bending driving portion 30 in the operation portion 7, thereby electrically bending the bending portion 12 (refer to FIG. 5). The two bending operation wires 26 or the two chains 26A are shown in the vertical or horizontal direction in FIGS. 4 and 5.

The bending driving portion 30 comprises the gear box 3 as a unit indicating the feature of the first embodiment and the bending and stretch mechanism portion 4 connected and fixed to the gear box 3 as a unit.

Referring to FIG. 5, the bending and stretch mechanism portion 4 comprises a sprocket 31 which winds the base end portion of the chain 26A for fixing and holding and which stretches or contracts the chain 26A, and a final gear 39 which is coaxially supported to the sprocket 31 and which transmits the driving force from a motor 32. The gear box 3 comprises the motor 32 for rotating the sprocket 31, and a decelerating gear train (also referred to as a gear train) 28 which transmits the driving force of the motor 32 to the final gear 39 and which decelerates the rotating speed of the motor 32 to generate large torque.

In (the bending driving portion 30 of) the gear box 3, a clutch 33 for disconnecting the driving force of the motor 32 is arranged between the sprocket 31 and the motor 32. Thus, (the bending driving portion 30 of) the gear box 3 disconnects the transmission of the driving force of the motor 32 by using the operation of the clutch 33 and enables a free operation of the angle. The clutch 33 is operated under the control of a control portion 35 arranged to the bending control device 100. The clutch 33 may manually be operated.

A signal line 32a is extended from the motor 32 in the gear box 3. The motor 32 in the gear box 3 receives a motor driving signal from a motor amplifier 34 arranged to the bending control device 100 via the signal line 32a in the universal cord 80. The motor amplifier 34 is connected to the control portion 35 and is controlled by the control portion 35.

The motor 32 comprises an encoder 36 which detects a rotating position as means for detecting the rotating position. A signal line 36a extending from the encoder 36 in the universal cord 80 is connected to the control portion 35. The encoder 36 outputs to the control portion 35, a rotating position signal indicating the detected rotating position of the motor 32.

The sprocket 31 in the bending and stretch mechanism portion 4 converts the rotation of the motor 32 into advancing and returning motion of the chain 26A. A potentiometer 37 for detecting the rotating position as the means for detecting the rotating position is connected to the sprocket 31. A signal line 37a extending from the potentiometer 37 in the universal cord 80 is connected to the control portion 35. Thus, the potentiometer 37 outputs to the control portion 35, a rotating position signal indicating the detected rotating position of the sprocket 31.

Reference numeral 38 denotes a switch for detecting a clutch operation and detects whether the clutch 33 is ON or OFF. A signal line 38a extending from the switch 38 for detecting the clutch operation in the universal cord 80 is connected to the control portion 35. Consequently, the switch 38 for detecting the clutch operation outputs to the control portion 35, a clutch operation signal indicating the detected operation of the clutch 33.

As mentioned above, the bending operation input portion 20 such as the joystick or the track ball is arranged to the grip portion 7a of the operating portion 7 in the electric bending endoscope 2. The signal line 20a extending from the bending operation input portion 20 in the universal cord 80 is connected to the control portion 35. As a result, the bending operation input portion 20 outputs to the control portion 35, a bending operation signal indicating the inputted bending operation.

The control portion 35 controls the motor amplifier 34 and drives the motor 32 in accordance with the bending operation signal from the bending operation input portion 20 based on the signals from the encoder 36 and the potentiometer 37 as the means for detecting the rotating position, thereby bending the bending portion 12.

To accomplish the above objects, the electric bending endoscope 2 used for the electric bending endoscope apparatus 1 with the above-mentioned structure is devised. The devised electric bending endoscope 2 will be described according to the first embodiment with reference to FIGS. 1 to 3.

According to the first embodiment, referring to FIG. 1, the electric bending endoscope 2 comprises the gear box 3 and the bending and stretch mechanism portion 4 forming the bending driving portion 30 for bending the bending portion 12 which are formed as units, respectively.

As mentioned above, the operating portion 7 (refer to FIG. 4) accommodates the gear box 3 and the bending and stretch mechanism portion 4.

Referring to FIGS. 2 and 3, the gear box 3 mainly comprises an outer gear frame 9 forming the external view of the gear box 3 and an inner gear frame 10 accommodated in the outer gear frame 9.

The inner gear frame 10 is made of a hard material, e.g., aluminum diecast, coaxially supports the motor 32, and builds in the encoder 36 and the potentiometer 37. Further, although not shown, the bending input portion 20 such as the joystick is fixed to the inner gear frame 10 via a connecting member on the top surface.

The decelerating gear train 28 (not shown in FIGS. 1 and 2) is arranged to the side surfaces on both sides of the inner gear frame 10. The driving force of the motor 32 is transmitted to the final gear 39 (refer to FIG. 5) in the bending and stretch mechanism portion 4 via the decelerating gear train 28.

As shown in FIGS. 2 and 3, the bending portion 12 comprises two motors 32, two encoders 36, and two potentiometers 37 sodas to be bent in the vertical direction or in the horizontal direction. Corresponding thereto, two decelerating gear trains 28, two final gears 39, and two sprockets 31 are provided. Further, according to the first embodiment, the bending portion 12 may be bent in the vertical direction or in the horizontal direction by providing one motor 32, one encoder 36, and one potentiometer 37 and, corresponding thereto, by one decelerating gear train 28, one final gear 39, and one sprocket 31.

The inner gear frame 10 has, on the top surface, a connecting and fixing member 8 for fixing the main frame 4A as a main part of the bending and stretch mechanism portion 4, which will be described later.

The outer gear frame 9 for accommodating the inner gear frame 10 has, on the bottom side of the inserting portion 6, a pair of an attaching hole 3B and a guide portion 3b as fixing means for connecting and fixing the bending and stretch mechanism portion 4 or the rotating shaft 4B as a unit. Further, the outer gear frame 9 has, on the side surface of the side of the bending and stretch mechanism portion 4 therein, an opening 3A for fitting to the bending and stretch mechanism portion 4. The attaching hole 3B guides and accommodates the rotating shaft 4B in the bending and stretch mechanism portion 4 via the guide portion 3b formed by being notched from the bottom surface side of the outer gear frame 9, and coaxially supports the rotating shaft 4B by the fitting of a positioning and fixing portion 5.

Referring to FIG. 1, the positioning and fixing portion 5 comprises: an attaching hole 5b for being fit into the rotating shaft 4B; a positioning piece 5a which is arranged to be projected to the inner surface side and which is R-shaped matching the inner peripheral surface of the attaching hole 3B; and at least three positioning pins 5c which are arranged in the outer-peripheral direction and which are fit into three positioning holes 3a formed near the attaching hole 3B of the outer gear frame 9.

When the rotating shaft 4B is connected and fixed to the gear box 3, the bending and stretch mechanism portion 4 is fit into the opening 3A, and the rotating shaft 4B is accommodated in the attaching hole 3B. Simultaneously, a base end portion of the rotating shaft 4B is fit into the attaching hole 5b of the fixing portion 5 from both sides thereof, and the positioning piece 5a is fit into the inner-peripheral portion of the attaching holes 3B so as to position the rotating shaft 4B to the gear box 3. Further, the positioning pin 5a is fit into the positioning hole 3a for the connection and fixing. Thus, the positioning operation is accurately performed and, thus, the final gear 39 coaxially arranged to the rotating shaft 4B is accurately engaged and connected to a low-speed gear train 28 (not shown in FIG. 1).

Referring to FIGS. 1 and 3, the bending stretch mechanism portion 4 has the rotating shaft 4B on a base end side thereof. A subframe 4C and the main frame 4A as the main frame member are attached near the center of the rotating shaft 4B. A pair of sprockets 31 and a pair of final gears 39 are arranged to both sides of the bending and stretch mechanism portion 4 to coaxially be supported. Therefore, the sprocket 31 and the final gear 39 are rotated integrally with the rotating shaft 4B. The rotating shaft 4B and the main frame 4A may not directly be fixed. That is, the rotating shaft 4B and the bending and stretch mechanism portion 4 are formed independently, and are formed as a part of the components of the gear box 3 which is detachably attached thereto. In this case, the main frame 4A is connected and fixed to the gear box 3 by using only the connecting and fixing member 8.

As shown in FIGS. 1 and 3, when the subframe 4C has two bending and stretch paths, the subframe 4C is arranged to partition the chain 26A for engagement with the sprocket 31. Upon bending the bending portion 12, the stretch operation of the chain 26A is accurately performed without the contact state of the chain 26A with each other.

The main frame 4A is the main frame member of the bending and stretch mechanism portion 4, and is plate-shaped with proper intensity. The main frame 4A is arranged to the subframe 4C at a predetermined interval. Referring to FIGS. 2 and 3, a bending portion 4a is formed near a portion for connecting the main frame 4A to the gear box 3 therein. The connecting and fixing member 8 is fixed to the bending portion 4a by screwing a screw 8b, thereby making the stronger connecting and fixing state of the main frame 4A and the gear box 3.

In this case, the other end portion of the connecting and fixing portion 8 is arranged to the top surface of the inner gear frame 10 as a hard member, and is fixed to the inner gear frame 10 by the screw operation of the screw 8a.

The connecting and fixing member 8 is made of a hard member such as a stainless member for the purpose of obtaining the intensity. Further, the intensity of the connecting and fixing member 8 may be improved by property changing the thickness or width.

According to the first embodiment, referring to FIGS. 1 and 2, the outer gear frame 9 covers the inner gear frame 10 which is built in. However, the outer gear frame 9 is not limited to this and may have neither top surface nor bottom surface of the outer gear frame 9 so as to expose the inner gear frame 10 to which the connecting and fixing member 8 is fixed so as to improve the maintenance and the assembly (refer to FIG. 8).

Next, a detailed description is given of the operations of the electric bending endoscope 2 with reference to FIGS. 1 to 3 and 6 and 7.

It is assumed that in the electric bending endoscope 2 shown in FIG. 2, the maintenance of the bending and stretch mechanism portion 4 is necessary and the bending and stretch mechanism portion 4 is replaced with a new one.

In this case, referring to FIG. 1, in the electric bending endoscope 2 according to the first embodiment, the gear box 3 and the bending and stretch mechanism portion 4 are structured as the units, respectively. Thus, referring to FIG. 2, the connecting and fixing member 8 for connecting and fixing the gear box 3 and the bending and stretch mechanism portion 4 is detached. That is, screws 8a and 8b for fixing the connecting and fixing member 8 to the inner gear frame 10 and the main frame 4A are rotated and detached, thereby detaching the connecting and fixing member 8.

Next, the bending and stretch mechanism portion 4 is detached from the gear box 3. Namely, the positioning and fixing portions 5 for fixing and holding the rotating shaft 4B of the bending and stretch portion 4 to the outer gear frame 9 is detached from the attaching holes 3B, thereby resetting the fixing and holding state of the rotating shaft 4B. Further, the rotating shaft 4B is moved to the opening side of the guide portion 3b, thereby resetting the engaging state between the low-speed gear train 28 in the gear box 3 and the final gear 39 in the bending and stretch mechanism portion 4. The bending and stretch mechanism portion 4 is completely detached from the gear box 3.

When the rotating shaft 4B is independently formed of the bending and stretch mechanism portion 4 and is formed as a part of the components of the gear box 3, the rotating shaft 4B is attached to the gear box 3 and only the connecting and fixing member 8 for connecting the gear box 3 to the main frame 4A of the bending and stretch mechanism portion 4 is detached, and the chain 26A is detached from the operation bending wire 26, thereby detaching the bending and stretch mechanism portion 4 from the gear box 3. That is, the bending and stretch mechanism portion 4 can be exchanged without the detachment of the rotating shaft 4B from the gear box 3.

The detached bending and stretch mechanism portion 4 is replaced with the new bending and stretch mechanism portion 4. Unlike the conventional technology by which the entire bending operation devices in the operating portion are resolved and the expensive gear box 3 is replaced though it has relatively long life, only the inexpensive bending and stretch mechanism portion 4 which has relatively a short life is easily detached and replaced.

Next, it is assumed that the exchanged new bending mechanism portion 4 is connected and fixed to the gear box 3. In this case, reversed operation of the detachment of the bending and stretch mechanism portion 4 may be executed.

That is, the rotating shaft 4B of the bending and stretch mechanism portion 4 is enclosed in the attaching hole 3B of the gear box 3, the base end portions on both sides of the rotating shaft 4B are fit into the attaching hole 5b of the positioning and fixing portion 5, and the positioning side 5a is fit into the inner-peripheral surface thereof, thereby positioning the rotating shaft 4B to the gear box 3. Further, the positioning pin 5 is fit into the positioning hole 3a, thereby executing the connection and fixing. Thus, the low-speed gear train 28 in the gear box 3 is engaged with and is connected to the final gear 39 in the bending and stretch mechanism portion 4.

When the rotating shaft 4B is formed independently of the bending and stretch mechanism portion 4 and is formed as a part of the components of the gear box 3, the rotating shaft 4B is attached to the gear box 3 and the chain 26A in the bending and stretch mechanism portion 4 is engaged with the sprocket 31 in the rotating shaft 4B and the chain 26A comes into contact with the operation bending wire 26. After that, the main frame 4A in the bending and stretch mechanism portion 3 is positioned to the gear box 3 and the bending and stretch mechanism portion 4 is connected and fixed to the gear box 3 by using the connecting and fixing member 8.

Preferably, the bending and stretch mechanism portion 4 is positioned and fixed to the gear box 3 at the position at which the loss is minimum when the driving force of the motor 32 is transmitted to the advance and return of the chain 26A and the bending operation wire 26.

According to the first embodiment, in order to satisfy the above requirements, referring to FIGS. 6 and 7, the bending and stretch mechanism portion 4 is positioned to the gear box 3 with much higher accuracy by using the positioning tool 14 for the connecting and fixing.

Referring to FIGS. 6 and 7, the positioning tool 14 is made of a cubic-shaped hard member having four planes of different heights, and comprises grooves 14A for regulating the gear box forming the first and second lower planes and grooves 14B for regulating the bending and stretch mechanism portion forming the third and fourth places higher than the first and second ones.

The groove 14A for regulating the gear box regulates three directions (x-, y-, and z-directions) of the gear box 3, and comprises: a first regulating surface 14a for slidably moving the gear box 3 and for regulating the vertical direction (z-direction) of the gear box 3; a second regulating surface 14b which is vertically to the first regulating surface 14a and which regulates the longitudinal direction (y-direction) of the gear box 3; and a third regulating surface 14e which is vertically arranged to the second regulating surface 14b and which regulates the horizontal direction (x-direction) of the gear box 3.

The groove 14B for regulating the bending and stretch mechanism portion comprises: a fourth regulating surface 14c which has the main frame 4A of the bending and stretch mechanism portion 4 thereon and which regulates and supports the gear box 3 in the vertical direction (z-direction); a fifth regulating surface 14d which is vertically to the fourth regulating surface 14c and which regulates the horizontal direction (x-direction) of the main frame 4A; and a sixth regulating surface 14f which regulates the longitudinal direction (y-direction) of the main frame 4A of the bending and stretch mechanism portion 4 to the gear box 3.

A regulating portion 4a for regulating the position of the main frame 4A to the gear box 3 is formed by making a part of the side surface of the edge of the main frame 4 contact with the sixth regulating surface 14f.

The height dimension of the fourth regulating surface 14c (difference in height from the first regulating surface 14a) is previously set at the best fixing position to the gear box 3.

It is assumed that the bending and stretch mechanism portion 4 is positioned to the gear box 3 by using the positioning tool 14 for the connecting and fixing. In this case, referring to FIG. 6, the gear box 3 is placed onto the groove 14A for regulating the gear box in the positioning tool 14, and the bending and stretch mechanism portion 4 fixed to the gear box 3 is placed onto the groove 14B for the bending and stretch mechanism of the positioning tool 14 by using the positioning and fixing portion 5.

In this state, the gear box 3 is slid onto the first regulating surface 14a and comes into contact with the second and third regulating surfaces 14d and 14e. Further, the main frame 4A of the bending and stretch mechanism portion 4 is slid onto the fourth regulating surface 14c and comes into contact with the fifth regulating surface 14d. Furthermore, the regulating portion 4a of the main frame 4A comes into contact with the sixth regulating surface 14f. Consequently, the main frame 4A of the bending and stretch mechanism portion 4 is positioned to the gear box 3 in the x-, y-, and z-directions thereof with ease and continuous high-accuracy, irrespective of the manual operation of the operator.

After that, the main frame 4A of the bending and stretch mechanism portion 4 is fixed to the gear box 3 by using the connecting and fixing member 8 so that the positioning state is maintained and the bending and stretch mechanism portion 4 is strongly connected to the gear box 3. Namely, one end portion of the connecting and fixing member 8 is fixed onto the inner gear frame 10 as the hard member by the screwing operation of the screw 8a, and the other end portion of the connecting and fixing member 8 is fixed onto the bending portion 4a of the main frame 4A by the screwing operation of the screw 8b.

The bending and stretch mechanism portion 4 is positioned to the gear box 3 at the position at which the loss becomes minimum upon transmitting the driving force of the motor 32 to the advance and return of the chain 26A and the bending operation wire 26, and the main frame 4A is strongly connected and fixed to the gear box 3.

Thus, since the bending and stretch mechanism portion 4 is connected and fixed to the gear box 3 at the best position, the transmission loss of the driving force is minimum and the motor 32 can be reduced in size as much as possible. As a result, the entire operating portions including the gear box 3 is reduced in size. Further, the gear rate of the low-speed train 28 in the gear box 3 is small and therefore the response performance of the bending operation is improved.

After completing the attachment of the bending and stretch mechanism portion 4, a connecting tube 17 is attached via a substrate 15 and a connecting member 16 which are arranged to the edge portion of the bending and stretch mechanism portion 4. Then, a cap 18 of the inserting portion 6 is fit into the other end side of the connecting tube 17 and the inserting portion 6 is attached by screwing a screw 19 via a screw hole 18a of the cap 18 and via a screw hole 17a of the connecting tube 17.

According to the first embodiment, the inserting portion 6, which is frequently used and to which external force is applied, is connected to the inner gear frame 10 as the hard member of the gear box 3 via the high-intensity members such as the cap 18, the connecting tube 17, the connecting member 16, the main frame 4A of the bending and stretch mechanism portion 4, and the connecting and fixing member 8. Thus, any external force (surplus force) is sufficiently absorbed during operating the electric bending endoscope 2. Then, the tolerance is excessively improved and the transmission loss can be minimum.

According to the first embodiment, the gear box 3 and the bending and stretch mechanism portion 4 are detachably formed as units, respectively. Thus, the simple structure improves the assembly and the maintenance performance and the maintenance costs are reduced in the electric bending endoscope.

The bending and stretch mechanism portion 4 is positioned and fixed to the gear box 3, by using the positioning tool 14, at the best position at which the transmission loss of the driving force becomes minimum. The motor 32 can be reduced in size and this contributes to the small size of the entire operating portions including the gear box 3. Further, the gear rate of the low-speed train 28 in the gear box 3 is small and therefore the response performance of the bending operation is improved.

Further, the main frame 4A of the bending and stretch mechanism portion 4 is connected and fixed to the inner gear frame 10 as the hard member via the connecting and fixing member 8. Therefore, any external force (surplus force) is sufficiently absorbed during the operation and the tolerance is excessively improved.

Second Embodiment

Figure 8:
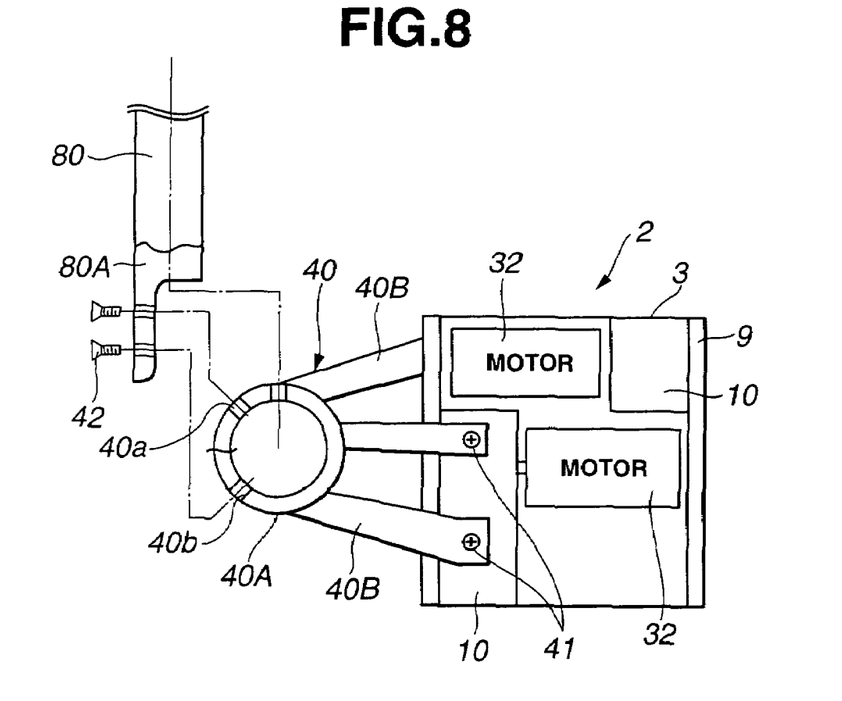
FIG. 8 is a diagram showing the structure of a gear box having a pin used for the electric bending endoscope according to a second embodiment of the present invention.
Figure 9:
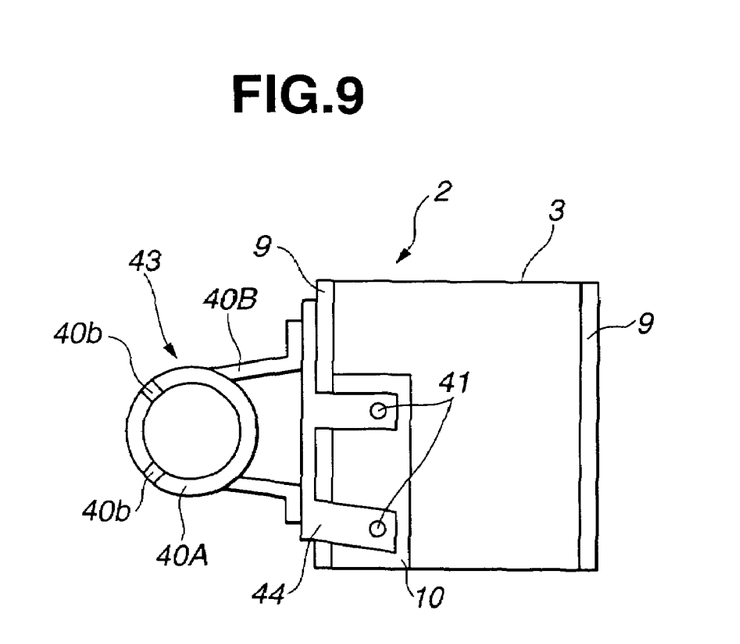
FIG. 9 is a diagram showing the structure of the gear box having the pin according to a modification of the pin shown in FIG. 8.

FIGS. 8 and 9 show an electric bending endoscope according to a second embodiment of the present invention. FIG. 8 is a diagram showing the structure of a gear box having a pin used for the electric bending endoscope according to the second embodiment. FIG. 9 is a diagram showing the structure of the gear box having a pin according to a modification of the pin shown in FIG. 8. Incidentally, the same components as those of the electric bending apparatus according to the first embodiment are designated by the same reference numerals in FIGS. 8 and 9, a description thereof is omitted, and only different portions are described.

According to the second embodiment, unlike the first embodiment, holding means for holding the universal cord 80 arranged in the operating portion 7 is fixed to the inner gear frame 19 of the gear box 3.

Specifically, referring to FIG. 8, the outer gear frame 9 of the gear box 3 is formed without the top surface and the bottom surface so that the inner gear frame 9 accommodated therein is exposed. Further, a stop tool 40 as holding means for holding the universal cord 80 is fixed to the inner gear frame 9 as the hard member, by using the screw 41.

In addition, referring to FIG. 8, the stop tool 40 comprises a ring-shaped holding portion 40A to which the universal cord 80 is fit by screwing a screw 42 and a fixing portion 40B which fixes the holding portion 40A to the inner gear frame 10 of the gear box 3 by at least three plate members or stick members.

The holding portion 40A has screw holes 40a and 40b at predetermined positions on the peripheral surface thereof. A connector 80A arranged to the edge portion of the universal cord 80 is fit and is held to the gear box 3 by screwing a screw 42 via a screw hole arranged to the connector 80A and the screw holes 40a and 40b.

Other structure is the same as that according to the first embodiment.

Therefore, according to the second embodiment, the external force (surplus force) is forcedly applied to the universal cord 80 during the operation. The universal cord 80 is fixed and held to the inner gear frame 10 as the hard member of the gear box 3 by using the stop tool 40, thereby absorbing the external force (surplus force) via the universal cord 80. Thus, the tolerance is remarkably improved and the engagement state (connecting state) is best held between the low-speed gear train 28 in the gear box 3 and the final gear 28 of the bending and stretch mechanism portion 4. Thus, the transmission loss of the driving force is reduced and the bending operation performance is preferably obtained. Other advantages are the same as those according to the first embodiment.

According to a modification of the second embodiment, the stop tool 40 as the holding means comprises the holding portion 40A into which the universal cord 80 is fit, a fixing portion 40B which is made of at least two plate members or stick members extended from the holding portion 40A, and a connecting member 44 which connects the fixing portion 40B by screwing a screw (not shown) and which fixes the fixing portion 40 to the inner gear frame 10 in the gear box 3. Thus, the stop tool 40 as the holding means may fix and hold the universal cord 80. In this case, the same advantages according to the first embodiment are obtained.

Third Embodiment

FIG. 10 shows an electric bending endoscope according to a third embodiment of the present invention, and is a cross-sectional view showing the structure of the electric bending endoscope, further showing the layout of a bending and stretch mechanism and switches in an operating portion provided for the electric bending endoscope, including a cut-off part according to the third embodiment of the present invention. Incidentally, the same components as those of the electric bending apparatus 2 shown in FIG. 10 according to the third embodiment are designated by the same reference numerals and are not described, and only different portions are described.

According to the third embodiment, in addition to the components according to the second embodiments, bending operation means 70 having a joystick 70a, various switches such as the air and water supply button 66, the suction button 67, and a scope switch (not shown) are connected to the inner gear frame 10 of the gear box 3 arranged in the operating portion 7, via mediating members 71 and 72.

Referring to FIG. 10, the outer gear frame 9 of the gear box 3 is formed without the top surface and the bottom surface such that the inner gear frame 9 accommodated therein is exposed. Further, fixed to the inner gear frame 10 as the hard member by screwing screws (not shown) are the mediating member 71 for fixing the joystick 70a and the mediating member 72 for fixing various switches such as the air and water supply button 66, the suction button 67, and a scope switch (not shown).

Other structures are the same as those according to the first and second embodiments.

According to the third embodiment, fixed and held to the inner gear frame 10 as the hard member of the gear box 3 are the joystick 70a to which the external force is forcedly applied during the operation of the endoscope including the bending operation and various switches such as the air and water supply button 66, the suction button 67, and the scope switch (not shown), via the mediating members 71 and 72, thereby absorbing the external force (surplus force) via the operating members. Similarly to the second embodiment, the tolerance is excessively improved. Further, the engagement state (connecting state) is best held between the low-speed gear train 28 in the gear box 3 and the final gear 28 of the bending and stretch mechanism portion 4. Thus, the transmission loss of the driving force is reduced and the preferable bending operation performance is obtained, that is, the equipment performance is improved.

Other advantages are the same as those according to the first and second embodiments.

In the electric bending endoscope 2 according to the third embodiment, the bending operability is improved. Technologies for improvement of the bending operability are disclosed here.

Referring to FIG. 10, in the electric bending endoscope 2 of the present invention, the center axis of the sprocket 31 of the bending and stretch mechanism portion 4 contact with the gear box 3 (not shown) is arranged to the front side of the operating portion 7 to which the various switches (the air and water supply button 66 and the suction button 67) are arranged, with respect to the center axis of the inserting portion 6. On the grip portion 7a in the operating portion 7, arranged to the chain 26A engaged with the sprocket 31 in the contact state, opposed thereto, are a pair of cylindrical members 65 having the slidability for bending the chain 26A along the center axis of the inserting portion 6. Thus, the center axis of the sprocket 31 is arranged to the front side of the operating portion 7, with respect to the center axis of the inserting portion 6. Therefore, a contact portion of a thumb base of the grip portion 7a in the operating portion 7 becomes a sloped surface as shown in FIG. 10, and the grip portion 7a is easily gripped.

Further, in the electric bending endoscope 2 shown in FIG. 10, an angle $\theta 1$ is formed between the center axis of the inserting portion 6 and the center axis of the joystick 70a as the bending operation input means 70 at the neutral position thereof, and is $(135°\pm150°)$. An inclined angle $\theta 2$ of the joystick 70*a* is ±30° from the center of the joystick 70*a*. The inclined center position of the joystick 70*a* is arranged in front of the operating portion 7 with respect to the center axis of the inserting portion 6. Thus, upon gripping the grip portion 7*a* substantially in the vertical state by the four fingers except for the thumb of the operator, the thumb operated by the joystick 70*a* is naturally placed to the position contact to the joystick 70*a*. Since the inclined angle θ2 is ±30° from the center of the joystick 70*a*, it is possible to prevent the deviation of the top position of the joystick 70*a* out of a thumb-operable range.

Further, in the electric bending endoscope 2 shown in FIG. 10, an angle θ3 is formed between the center axis of the joystick 70*a* at the neutral position thereof and the operation direction of the operation switches including at least the air and water supply button 66 and the suction button 67. The angle θ3 is 30° or more.

When the angle θ3 is not more than 30° where the angle θ3 is formed between the center axis of the joystick 70*a* operated by the thumb at the neutral position thereof and the operation direction of the operation switches by the index finger or middle finger, the force is applied to the index finger and the middle finger upon operating the joystick 70*a* by the thumb. The opposed operation switches (the air and water supply button 66 and the suction button 67) are pressed irrespectively of the operator's desire. Alternatively, upon operating the operation switches by the middle finger or the index finger, the joystick 70*a* might be pressed by the thumb though he does not desire it. However, in the example, as mentioned above, the angle θ3 of 30° or more is formed between the center axis of the joystick 70*a* at the neutral position thereof and the operation direction of the operation switch including at least the air and water supply button 66 and the suction button 67. Thus, both upon operating the joystick 70*a* by the thumb and upon operating the operation switches by the middle finger or the index finger, the above operation results in reducing the danger for operating the operation switches (the air and water supply button 66 and the suction button 67) arranged to the opposed surface of the operating portion or the joystick 70*a* though he does not desire this.

The above technologies improve the operability of the electric bending endoscope 2.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An electric bending endoscope comprising:
   a bending portion arranged to an inserting portion;
   a first unit which has a frame unit which holds a motor that generates driving force for bending the bending portion, the frame unit being connected to a cord for supplying a signal for driving the motor from a bending control device;
   a second unit which is separable from the first unit and which has a transmitting member for transmitting the driving force of the motor to the bending portion, the second unit having a main frame to which is connected the inserting portion; and
   a buffering member that is a plate member, the buffering member being connected to the frame unit at a first portion of the plate member and to the main frame at a second portion of the plate member, an intermediate portion between the first portion and the second portion of the plate member being arranged to traverse across a junction between the first unit and the second unit, the buffering member absorbing a force applied to the inserting portion by an external operation between the first portion connected to the frame unit and the second portion connected to the main frame, wherein the first unit has a frame unit which comprises an inner frame for holding the motor and an outer frame for holding the inner frame, and the buffering member further includes a fixing member which fixes the inner frame of the first unit and a main frame arranged to the second unit and the frame unit and the main frame are fixed via the fixing member by using a positioning tool for positioning in a three-axial direction.

2. The electric bending endoscope according to claim 1, further comprising an operating portion connected to the first unit for operating the electric bending endoscope,
   wherein a wheel is arranged to the driving force transmitting member of the second unit, and a rotating shaft of the wheel is arranged in front of the operating portion on a side cross-section of the operating portion in the electric bending endoscope, with respect to a central axis of the inserting portion.

3. An electric bending endoscope comprising:
   a bending portion arranged to an inserting portion;
   a first unit which has a frame unit which holds a motor that generates driving force for bending the bending portion, the frame unit being connected to a cord for supplying a signal for driving the motor from a bending control device;
   a second unit which is separable from the first unit and which has a transmitting member for transmitting the driving force of the motor to the bending portion, the second unit having a main frame to which is connected the inserting portion; and
   a buffering member that is a plate member, the buffering member being connected to the frame unit at a first portion of the plate member and to the main frame at a second portion of the plate member, an intermediate portion between the first portion and the second portion of the plate member being arranged to traverse across a junction between the first unit and the second unit, the buffering member absorbing a force applied to the inserting portion by an external operation between the first portion connected to the frame unit and the second portion connected to the main frame, the buffering member further including a fixing member, wherein the frame unit and the main frame are fixed via the fixing member by using a positioning tool for positioning in a three-axial direction.

\* \* \* \* \*